(12) United States Patent
Gribble et al.

(10) Patent No.: US 8,921,419 B2
(45) Date of Patent: Dec. 30, 2014

(54) TRITERPENOIDS AND COMPOSITIONS CONTAINING THE SAME

(75) Inventors: Gordon W. Gribble, Lebanon, NH (US); Liangfeng Fu, West Lebanon, NH (US); Michael B. Sporn, Tunbridge, VT (US); Karen T. Liby, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 280 days.

(21) Appl. No.: 13/466,456

(22) Filed: May 8, 2012

(65) Prior Publication Data

US 2013/0303607 A1 Nov. 14, 2013

(51) Int. Cl.
| | | |
|---|---|---|
| A61K 31/215 | (2006.01) | |
| C07C 69/753 | (2006.01) | |
| C07J 63/00 | (2006.01) | |
| A61K 31/56 | (2006.01) | |

(52) U.S. Cl.
CPC ............. *C07J 63/008* (2013.01); *A61K 31/56* (2013.01)
USPC ........................................ 514/510; 560/116

(58) Field of Classification Search
CPC ............................. C07J 63/008; A61K 31/56
USPC ........................................ 514/510; 560/116
See application file for complete search history.

(56) References Cited

U.S. PATENT DOCUMENTS

| | | | |
|---|---|---|---|
| 6,326,507 B1 | 12/2001 | Gribble et al. | 558/415 |
| 6,552,075 B2 | 4/2003 | Gribble et al. | 514/522 |
| 6,974,801 B2 | 12/2005 | Honda et al. | 514/25 |
| 7,288,568 B2 | 10/2007 | Gribble et al. | 514/519 |
| 7,863,327 B2 | 1/2011 | Gribble et al. | 514/521 |
| 7,915,402 B2 | 3/2011 | Anderson et al. | 540/519 |
| 7,943,778 B2 | 5/2011 | Jiang et al. | 548/247 |
| 8,034,955 B2 | 10/2011 | Gribble et al. | 548/241 |
| 2008/0233195 A1 | 9/2008 | Spoorn et al. | 424/486 |
| 2009/0048204 A1 | 2/2009 | Walling et al. | 514/49 |
| 2009/0060873 A1 | 3/2009 | Sporn et al. | 424/85.6 |
| 2009/0326063 A1 | 12/2009 | Sporn et al. | 514/529 |
| 2010/0048887 A1 | 2/2010 | Anderson et al. | 540/8 |
| 2010/0048892 A1 | 2/2010 | Anderson et al. | 544/154 |
| 2010/0048911 A1 | 2/2010 | Jiang et al. | 548/250 |
| 2011/0245206 A1 | 10/2011 | Jiang et al. | 514/112 |
| 2011/0245233 A1 | 10/2011 | Anderson et al. | 514/212.04 |

FOREIGN PATENT DOCUMENTS

| | | | |
|---|---|---|---|
| CN | 101117348 | * | 2/2008 |
| WO | WO 2004/064723 A2 | | 8/2004 |
| WO | WO 2005/046732 A2 | | 5/2005 |
| WO | WO 2008/064132 A2 | | 5/2008 |
| WO | WO 2008/136838 A1 | | 11/2008 |
| WO | WO 2009/023232 A1 | | 2/2009 |

OTHER PUBLICATIONS

Hartwig, J. F. "Carbon-Heteroatom Bonding-Forming Reductive Eliminations of Amines, Ethers, and Sulfides" Accounts of Chemical Research 1998 31(12):852-860.
Hartwig, J. F. "Transition Metal Catalyzed Synthesis of Arylamines and Aryl Ethers from Aryl Halides and Triflates: Scope and Mechanism" Angewandate Chemie International Edition 1998 37:2047-2067.
Hartwig, J. F. "Approaches to Catalyst Discovery. New Carbon-Heteroatom and Carbon—Carbon Bond Formation" Pure and Applied Chemistry 1999 71(8):1417-1423.
Honda et al. "New Enone Derivatives of Oleanolic Acid and Ursolic Acid as Inhibitors of Nitric Oxide Production in Mouse Marcophages" Bioorganic & Medicinal Chemistry Letters 1997 7(13):1623-1628.
Honda et al. "Design and Synthesis of 2-Cyano-3,12-Dioxoolean-1,9-Dien-28-OIC Acid, A Novel and Highly Active Inhibitor of Nitric Oxide Production in Mouse Marcophages" Bioorganic & Medicinal Chemistry Letters 1998 8:2711-2714.
King et al. "Highly General Stereo-, Regio-, and Chemo-Selective Synthesis of Terminal and Internal Conjugated Enynes by the Pd-Catalysed Reaction of Alkynylzinc Reagents with Alkenyl Halides" Journal of the Chemical Society, Chemical Communications 1977 19:683-684.
Kosugi et al. "Reactions of Allyltin Compounds III. Allylation of Aromatic Halides with Allyltributyltin in the Presence of Tetrakis(Triphenylphosphine)Palladium(0)" Chemistry Letters 1977:301-302.
Milstein, D. and Stille, J. K. "A General, Selective, and Facile Method for Ketone Synthesis from Acid Chlorides and Organotin Compounds Catalyzed by Palladium" Journal of the American Chemical Society 1978 100(11):3636-3638.
Miyaura et al. "A New Stereospecific Cross-Coupling by the Palladium-Catalyzed Reaction of 1-Alkenylboranes with 1-Alkenyl or 1-Alkynyl Halides" Tetrahedron Letters 1979 36:3437-3440.
Miyaura, N. and Suzuki, A. "Palladium-Catalyzed Cross-Coupling Reactions of Organoboron Compounds" Chemical Reviews 1995 95(7):2457-2483.
Muci, A. R. and Buchwald, S. L. "Practical Palladium Catalysts for C—N and C—O Bond Formation" Topics in Current Chemistry 2002 219:133-209.
Porcheddu et al. "Microwave-Assisted Synthesis of Isonitriles: A General Simple Methodology" Journal of Organic Chemistry 2005 70:2361-2363.
Sonogashira et al. "A Convenient Synthesis of Acetylenes: Catalytic Substitutions of Acetylenic Hydrogen with Bromoalkenes, Iodoarenes, and Dromopyridines" Tetrahedron Letters 1975 50:4467-4470.
Wolfe et al. "Rational Development of Practical Catalysts for Aromatic Carbon-Nitrogen Bond Formation" Accounts of Chemical Research 1998 31(12):805-818.
Yang, B. H. and Buchwald, S. L. "Palladium-Catalyzed Amination of Aryl Halides and Sulfonates" Journal of Organometallic Chemistry 1999 576:125-146.

* cited by examiner

*Primary Examiner* — Barbara P Badio
(74) *Attorney, Agent, or Firm* — Licata & Tyrrell P.C.

(57) ABSTRACT

The present invention provides triterpenoids produced from natural compounds such as oleanolic acid, ursolic acid, betulinic acid, and hederagenin.

2 Claims, No Drawings

TRITERPENOIDS AND COMPOSITIONS CONTAINING THE SAME

BACKGROUND OF THE INVENTION

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn & Roberts (1986) *J. Clin. Invest.* 78:329-332; Ohshima & Bartsch (1994) *Mutat. Res.* 305:253-264). The enzymes that mediate the constitutive synthesis of nitric oxide and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada, et al. (1991) *Pharmacol. Rev.* 43:109-142; Nathan & Xie (1994) *Cell* 78:915-918; Siebert & Masferrer (1994) *Receptor* 4(1):17-23; Tamir & Tannebaum (1996) *Biochim. Biophys. Acta* 1288:F31-F36). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang, et al. (1994) *Cancer Res.* 54:701-708; Nishino, et al. (1988) *Cancer Res.* 48:5210-5215). However, the biological activity of these naturally occurring molecules is relatively weak, and therefore the synthesis of new analogs to enhance their potency has been undertaken (see, e.g., Honda, et al. (1997) *Bioorg. Med. Chem. Lett.* 7:1623-1628; Honda, et al. (1998) *Bioorg Med Chem. Lett.* 8(19):2711-2714).

In this respect, U.S. Pat. No. 6,326,507, U.S. Pat. No. 6,552,075, U.S. Pat. No. 7,288,568, U.S. Pat. No. 7,863,327, U.S. Pat. No. 8,034,955, US 2009/0060873, US 2009/0048204, WO 2008/136838 and WO 2009/023232 teach the use of 2-cyano-3,12-dioxooleana-1,9(11)-dien-28-oic acid (CDDO), and derivatives thereof such as 2-cyano-3,12-dioxoolean-1,9(11)-dien-28-oic acid methyl ester (CDDO-Me) and amide derivatives, for the treatment of diseases such as cancer, Alzheimer's disease, Parkinson's disease, inflammatory bowel diseases, and multiple sclerosis. Similarly, U.S. Pat. No. 6,974,801 and WO 2004/064723 teach the use of 2-cyano-3,12-dioxooleana-1,9(11)-dien-28-onitrile (CNDDO), 1-(2-cyano-3,12-dioxooleana-1,9(11)-dien-28-oyl) imidazole (CDDO-Im), 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole in the prevention or treatment of cancer, Alzheimer's disease, Parkinson's disease, multiple sclerosis, rheumatoid arthritis, and other inflammatory diseases. Furthermore, the use of triterpenoids such as CDDO, CDDO-Me, CDDO-Im, and CDDO-Ethylamide in stimulating the growth and repair of bone and cartilage (US 2008/0233195 and WO 2008/064132) as well as in inhibiting HIV-1 replication (WO 2005/046732) has been described. US 2009/0326063 further teaches the use of synthetic triterpenoids in the prevention and treatment of renal/kidney disease, insulin resistance/diabetes, fatty liver disease, and/or endothelial dysfunction/cardiovascular disease.

Combination therapies of CDDO or CDDO-Me and a chemotherapeutic agent, immunosuppressive agent, or proteasome inhibitor are described in U.S. Pat. No. 7,435,755, U.S. Pat. No. 7,795,305, US 2009/0018146, US 2009/0048205, WO 2002/047611 and WO 2009/023845 for the treatment of cancer and graft versus host disease. Moreover, formulations for improved oral bioavailability of CDDO-Me are disclosed in WO 2010/093944.

Given the activity of CDDO and CDDO-Me, additional oleanolic acid derivatives have been developed for use in treating cancer, cardiovascular disease, neurodegenerative disease, renal/kidney disease, diabetes, arthritis and inflammatory conditions such as obesity, hypertension, atherosclerosis, coronary heart disease, stroke, peripheral vascular disease, hypertension, nephropathy, neuropathy, myonecrosis, ulcerative colitis, Crohn's disease, irritable bowel syndrome, retinopathy and metabolic syndrome. See U.S. Pat. No. 7,915,402, U.S. Pat. No. 7,943,778, US 2010/0048887, US 2010/0048892, US 2010/0048911, US 2011/0245206 and US 2011/0245233.

In view of the therapeutic activities of this class of triterpenoids, it would be advantageous to have compounds with improved activity.

SUMMARY OF THE INVENTION

The present invention is a triterpenoid compound of Formula I, II, VI, VII, VIII, IX, X, XI, XII, XIII, XIV, XV, or XVI, as defined herein and a pharmaceutical composition containing the same.

DETAILED DESCRIPTION OF THE INVENTION

Triterpenoids, including CDDO-Me derivatives, have now been developed. The triterpenoids described herein can be used in the treatment of disease, especially inflammatory diseases. Compounds particularly embraced by this invention have the structure of Formula I, which includes hydrates, isomers, prodrugs or pharmaceutically acceptable salts of Formula I:

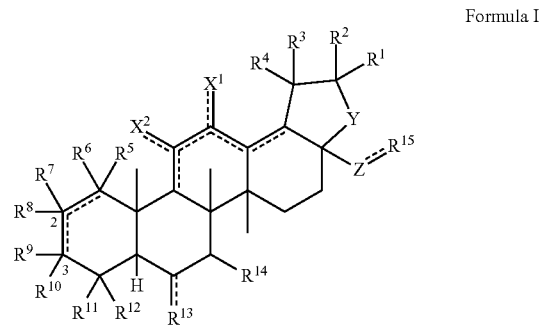

Formula I wherein,
at least one of $X^1$ and $X^2$ is $OR^a$, $NR^aR^b$, or $SR^a$, and the other of $X^1$ and $X^2$ is hydrogen, $OR^a$, $NR^aR^b$, or $SR^a$ wherein
$R^a$ is a hydrogen, cyano, —CF$_3$, nitro, amino, or substituted or unsubstituted heteroaryl group;
$R^b$ is hydrogen, hydroxyl, alkyl, aryl, aralkyl, acyl, alkoxy, aryloxy, acyloxy, alkylamino, arylamino, amido, or a substituted version of any of these groups;
or a substituent convertible in vivo to hydrogen;
provided that $R^a$ is absent when the atom to which it is bound is part of a double bond, further provided that when $R^a$ is absent the atom to which it is bound is part of a double bond;
Y is CH$_2$ or CH$_2$—CH$_2$;
Z is a covalent bond, —C(=O)—, alkanediyl, alkenediyl, alkynediyl, or a substituted version of any of these groups;
the dashed bonds can be independently present or absent;
$R^1$, $R^2$, $R^3$ and $R^4$ are each independently a hydrogen, hydroxyl, alkyl, substituted alkyl, alkoxy or substituted alkoxy group;
at least one of $R^5$, $R^6$, $R^7$, $R^8$, $R^9$ or $R^{10}$ is independently —OMs, —CH$_2$OMs, —C(=O) C≡CR$^a$, —C≡CCO$_2$R$^a$, —C≡CSO$_2$R$^a$, —C≡CC(=O)R$^a$ or —SO$_2$R$^a$, or
$R^5$ and $R^6$, or $R^7$ and $R^8$, or $R^9$ and $R^{10}$ are together or =CR$^c$R$^d$, wherein
$R^c$ is hydrogen or alkylthiyl, and
$R^d$ is hydrogen, halo, alkylthiyl, or substituted or unsubstituted alkylsulfonyl or alkylsulfonyl-O—;
the remainder of $R^5$, $R^6$, $R^7$, $R^8$, $R^9$ and $R^{10}$ are independently hydrogen, hydroxyl, halo, cyano, =O, —C≡CR$^a$, —CO$_2$R$^a$, —COR$^a$, alkyl, alkenyl, alkynyl, aryl, aralkyl, heteroaryl, heteroaralkyl, acyl, alkoxy, aryloxy, acyloxy, alkylamino, arylamino, nitro, amino, amido, —C(O) R$^e$ or a substituted version of any of these groups, wherein
$R^e$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;
$R^{11}$ and $R^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or
$R^{11}$ and $R^{12}$ are taken together and are alkanediyl, alkanediyl, arenediyl, alkoxydiyl, alkenyloxydiyl, alkylaminodiyl, alkenylaminodiyl, or alkenylaminooxydiyl;
$R^{13}$ is hydrogen, hydroxy or oxo;
$R^{14}$ is hydrogen or hydroxyl; and
$R^{15}$ is
a hydrogen, hydroxyl, —NR$^f$R$^g$, cyano, halo, azido, phosphate, 1,3-dioxoisoindolin-2-yl, mercapto, silyl or —COOH group,
substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups,
a —CO$_2$Me, carbonyl imidazole, —CO-D-Glu(OAc)$_4$, —CONH$_2$, —CONHNH$_2$, —CONHCH$_2$CF$_3$, or —C(=O)-heteroaryl group, or
Z and $R^{15}$ form a three to seven-membered ring, such that Z and $R^{15}$ are further connected to one another through one or more of —O— and alkanediyl, further wherein Z is —CH— and $R^{15}$ is —CH$_2$— or Z, $R^{15}$, and carbon numbers 13, 17 and 18 form a ring such that $R^{15}$ is bound to carbon 13, wherein Y is methanediyl or substituted methanediyl and $R^{15}$ is —O—, wherein
$R^f$ and $R^g$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups.

In certain embodiments, the bond between $C_2$ and $C_3$ in the A-ring is a double bond. In other embodiments, the bond between $C_2$ and $C_3$ in the A-ring is a single bond.

In some embodiments, the compound of the invention is a dimer as represented by the Formula II,

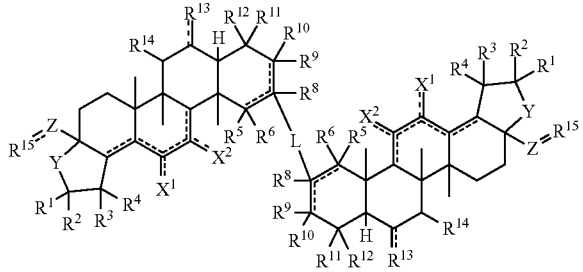

Formula II wherein $X^1$, $X^2$, Y, Z, $R^1$, $R^2$, $R^3$, $R^4$, $R^8$, $R^9$, $R^{11}$, $R^{12}$, $R^{13}$, $R^{14}$ and $R^{15}$ are as defined for Formula I and L is —C≡C—R—C≡C—, —C(=O)—, —C≡C—, —C≡C—N(—R)—, —C(=O)—N(—R)—, —C≡C—C(=O)—, Ar—C(=O)—, or —C≡C—C(=O)—Ar—, wherein R is hydrogen, or an alkyl, aryl, alkenyl, or alkynyl group. Exemplary dimers include compounds 10-17.

In yet other embodiments, the compound of the invention has the structure as set forth in Formulae VI-XVI. In particular embodiments, the triterpenoid compound of the invention is a compound selected from compound 18-75.

As used herein, "hydrogen" means —H; "hydroxyl" means —OH; "oxo" means =O; "halo" or "halogen" means independently —F, —Cl, —Br or —I; "hydroxyamino" means —NHOH; "nitro" means —NO$_2$; "cyano" means —CN; "azido" means —N$_3$; "mercapto" means —SH; "thio" means =S; "sulfonyl" means —S(O)$_2$— (see additional definitions of groups containing the term sulfonyl, e.g., alkylsulfonyl); and "silyl" means —SiH$_3$ (see additional definitions of group(s) containing the term silyl, e.g., alkylsilyl).

For the groups below, the following parenthetical subscripts further define the groups as follows: "(Cn)" defines the exact number (n) of carbon atoms in the group. For example, "C$_1$-C$_{15}$-alkoxy" designates those alkoxy groups having from 1 to 15 carbon atoms (e.g., 1, 2, 3, 4, 5, 6, 7, 8, 9, 10, etc. or any range derivable therein (e.g., 3-10 carbon atoms)).

The term "alkyl" refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$) CH$_2$CH$_3$, —CH$_2$CH (CH$_3$)$_2$, —(CH$_3$)$_3$, —CH$_2$C(CH$_3$)$_3$, cyclobutyl, cyclopentyl, cyclohexyl, and cyclohexylmethyl are non-limiting examples of alkyl groups.

The term "alkanediyl" refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$ CH$_2$—, and —CH$_2$CH$_2$CH$_2$— are non-limiting examples of alkanediyl groups.

The term "alkenyl" refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$, —CH=CHCH$_3$, —CH=CHCH$_2$CH$_3$, —CH$_2$CH=CH$_2$, —CH$_2$CH=CHCH$_3$, and —CH=CH— C$_6$H$_5$.

The term "alkenediyl" refers to a nonaromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$— are non-limiting examples of alkenediyl groups.

The term "alkynyl" refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups.

The term "alkynediyl" refers to a nonaromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups.

The term "aryl" refers to a monovalent group with an aromatic carbon atom as the point of attachment, said carbon atom forming part of a six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —C$_6$H$_4$CH(CH$_3$)$_2$, —C$_6$H$_4$CH(CH$_2$)$_2$, methylethylphenyl, vinylphenyl, naphthyl, and the monovalent group derived from biphenyl.

The term "arenediyl" refers to a divalent group, wherein the arenediyl group is attached with two α-bonds, with two aromatic carbon atoms as points of attachment, said carbon atoms forming part of one or more six-membered aromatic ring structure(s) wherein the ring atoms are all carbon, and wherein the monovalent group is composed of carbon and hydrogen. Non-limiting examples of arenediyl groups include:

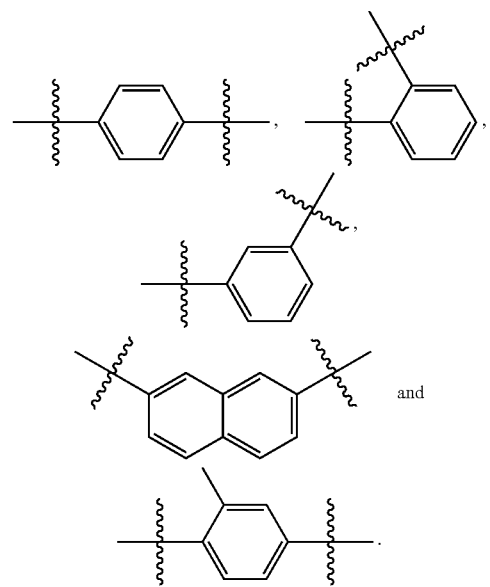

The term "aralkyl" refers to the monovalent group -alkanediyl-aryl, in which the terms alkanediyl and aryl are each used in a manner consistent with the definitions provided above. Non-limiting examples of aralkyls include 1-phenyl-ethyl, 2-phenyl-ethyl, indenyl and 2,3-dihydro-indenyl, provided that indenyl and 2,3-dihydro-indenyl are only, examples of aralkyl in so far as the point of attachment in each case is one of the saturated carbon atoms.

The term "heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms).

The term "heteroaralkyl" refers to the monovalent group -alkanediyl-heteroaryl, in which the terms alkanediyl and heteroaryl are each used in a manner consistent with the definitions provided above. Non-limiting examples of aralkyls include pyridylmethyl, and thienylmethyl.

The term "acyl" refers to a monovalent group with a carbon atom of a carbonyl group as the point of attachment, further having a linear or branched, cyclo, cyclic or acyclic structure. The groups, —CHO, —C(=O)CH$_3$, —C(=O)CH$_2$CH$_3$, —C(=O)CH$_2$CH$_2$CH$_3$, —C(=O)CH(CH$_3$)$_2$, —C(=O)CH(CH$_2$)$_2$, —C(=O) C$_6$H$_5$, —C(=O)C$_6$H$_4$CH$_3$, and —C(=O)C$_6$H$_4$CH$_2$CH$_3$ are non-limiting examples of acyl groups. The term "acyl" therefore encompasses, but is not limited to groups sometimes referred to as "alkyl carbonyl" and "aryl carbonyl" groups.

The term "alkoxy" refers to the group —OR, in which R is an alkyl, as that term is defined herein. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl.

Similarly, the terms "alkenyloxy," "alkynyloxy," "aryloxy," "aralkoxy," "heteroaryloxy," "heteroaralkoxy" and "acyloxy," refer to groups, defined as —OR, in which R is alkenyl, alkynyl, aryl, aralkyl, heteroaryl, heteroaralkyl and acyl, respectively, as those terms are defined above.

The term "alkoxydiyl" refers to a non-aromatic divalent group, wherein the alkoxydiyl group is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone. The groups, —O—CH$_2$CH$_2$—, —CH$_2$—O—CH$_2$CH$_2$—, —O—CH$_2$CH$_2$—O— and —O—CH$_2$—O— are non-limiting examples of alkoxydiyl groups.

The term "alkenyloxydiyl" refers to a divalent group that is nonaromatic prior to attachment, wherein the alkenyloxydiyl group is attached with two α-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone. The groups, —O—CH=CH—, —O—CH=CHO— and —O—CH=CHCH$_2$— are non-limiting examples of alkenyloxydiyl groups.

The term "amino" refers to a moiety of the formula —NRR', wherein R and R' are independently hydrogen, alkyl, cycloalkyl, heterocycloalkyl, aryl or heteroaryl.

The term "alkylamino" refers to the group —NHR, in which R is an alkyl, as that term is defined above. Non-limiting examples of alkylamino groups include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl.

Similarly, the terms "alkoxyamino," "alkenylamino," "alkynylamino," "arylamino," "aralkylamino," "heteroarylamino," "heteroaralkylamino," and "alkylsulfonylamino" refer to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$.

The term "dialkylamino" refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include —NHC(CH$_3$)$_3$, —N(CH$_3$) CH$_2$CH$_3$, —N(CH$_2$CH$_3$)$_2$, N-pyrrolidinyl, and N-piperidinyl.

The term "alkylaminodiyl" refers to a non-aromatic divalent group, wherein the alkylaminodiyl group is attached with two (3-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone. The groups, —NH—CH$_2$CH$_2$—, —CH$_2$—NH—CH$_2$CH$_2$—, —NH—CH$_2$CH$_2$—NH— and —NH—CH$_2$—NH— are non-limiting examples of alkylaminodiyl groups.

The term "alkenylaminodiyl" refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen. The groups —NH—CH=CH—, —NH—CH=N— and —NH—CH=CH—NH— are non-limiting examples of alkenylaminodiyl groups.

The term "alkenylaminooxydiyl" refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone. The group —O—CH=N—, is a non-limiting example of an alkenylaminooxydiyl group.

The term "amido" (acylamino) refers to the group —NHR, in which R is acyl, as that term is defined herein. A non-limiting example of an acylamino group is —NHC(=O)CH$_3$.

The term "alkylthio" refers to the group —SR, in which R is an alkyl, as that term is defined above. Non-limiting examples of alkylthio groups include —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl.

Similarly, the terms "alkenylthio," "alkynylthio," "arylthio," "aralkylthio," "heteroarylthio," "heteroaralkylthio" and "acylthio" refer to groups, defined as —SR, in which R is alkenyl, alkynyl, aryl, aralkyl, heteroaryl, heteroaralkyl and acyl, respectively, as those terms are defined above.

The term "thioacyl" refers to a monovalent group with a carbon atom of a thiocarbonyl group as the point of attachment, further having a linear or branched, cyclo, cyclic or acyclic structure. The groups —CHS, —C(=S)CH$_3$, —C(=S)CH$_2$CH$_3$, —C(=S)CH$_2$CH$_2$CH$_3$, —C(=S)CH(CH$_3$)$_2$, —C(=S)CH(CH$_2$)$_2$, —C(=S)C$_6$H$_5$, —C(=S)C$_6$H$_4$CH$_3$, —C(=S)C$_6$H$_4$CH$_2$CH$_3$, —C(=S)C$_6$H$_3$(CH$_3$)$_2$, and —C(=S)CH$_2$C$_6$Hs, are non-limiting examples of thioacyl groups. The term "thioacyl" therefore encompasses, but is not limited to, groups sometimes referred to as "alkyl thiocarbonyl" and "aryl thiocarbonyl" groups.

The term "alkylsulfonyl" refers to the group —S(=O)$_2$R, in which R is an alkyl, as that term is defined above. Non-limiting examples of alkylsulfonyl groups include: —S(=O)$_2$CH$_3$, —S(=O)$_2$CH$_2$CH$_3$, —S(=O)$_2$CH$_2$CH$_2$CH$_3$, S(=O)$_2$CH(CH$_3$)$_2$, —S(=O)$_2$CH(CH$_2$)$_2$, —S(=O)$_2$-cyclopentyl, and —S(=O)$_2$-cyclohexyl.

Similarly, the terms "alkenylsulfonyl," "alkynylsulfonyl," "arylsulfonyl," "aralkylsulfonyl," "heteroarylsulfonyl," and "heteroaralkylsulfonyl" refer to groups, defined as —S(O)$_2$R, in which R is alkenyl, alkynyl, aryl, aralkyl, heteroaryl, and heteroaralkyl, respectively, as those terms are defined above.

The term "alkylsulfinyl" refers to the group —S(=O)R, in which R is an alkyl, as that term is defined above. Non-limiting examples of alkylsulfinyl groups include —S(=O)CH$_3$, —S(=O)CH$_2$CH$_3$, —S(=O)CH$_2$CH$_2$CH$_3$, —S(=O)CH(CH$_3$)$_2$, —S(=O)CH(CH$_2$)$_2$, —S(=O)-cyclopentyl, and —S(=O)-cyclohexyl.

Similarly, the terms "alkenylsulfinyl," "alkynylsulfinyl," "arylsulfinyl," "aralkylsulfinyl," "heteroarylsulfinyl" and "heteroaralkylsulfinyl" refer to groups, defined as —S(=O)R, in which R is alkenyl, alkynyl, aryl, aralkyl, heteroaryl, and heteroaralkyl, respectively, as those terms are defined above.

The term "alkylammonium" refers to a group, defined as —NH$_2$R$^+$, —NHRR'$^+$, or —NRR'R''$^+$, in which R, R' and R'' are the same or different alkyl groups, or any combination of two of R, R' and R'' can be taken together to represent an alkanediyl. Non-limiting examples of alkylammonium cation groups include —NH$_2$(CH$_3$)$^+$, —NH$_2$(CH$_2$CH$_3$)+, —NH$_2$(CH$_2$CH$_2$CH$_3$)+, —NH(CH$_3$)$_2^+$, —NH(CH$_2$CH$_3$)$_2^+$, —NH(CH$_2$CH$_2$CH$_3$)$^+$, —N(CH$_3$)$_3^+$, —N(CH$_3$)(CH$_2$CH$_3$)$_2^+$, —N(CH$_3$)$_2$(CH$_2$CH$_3$)$^+$, —NH$_2$C(CH$_3$)$_3^+$, —NH(cyclopentyl)$_2^+$, and —NH$_2$(cyclohexyl)$^+$.

The term "alkylthiyl" refers to the group —SR. Non-limiting examples of alkylthiyl groups include —S(CH$_3$), —S(CH$_2$CH$_3$), —S(CH$_2$CH$_2$CH$_3$), —S(cyclopentyl), and —S(cyclohexyl).

The term "alkylsilyl" refers to a monovalent group, defined as —SiH$_2$R, —SiHRR', or —SiRR'R'', in which R, R' and R'' can be the same or different alkyl groups, or any combination of two of R, R' and R'' can be taken together to represent an alkanediyl. The groups —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups.

The term "alkylphosphonyl" refers to the group —OPO(OR)$_2$, where R is alkyl, as defined herein.

The term "alkylphosphate" refers to the group —OP(=O)(OH)(OR), in which R is an alkyl, as that term is defined above. Non-limiting examples of alkylphosphate groups include —OP(=O)(OH)(OMe) and —OP(=O)(OH)(OEt).

The term "dialkylphosphate" refers to the group —O(=O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include —OP(=O)(OMe)$_2$, —OP(=O)(OEt)(OMe) and —OP(=O)(OEt)$_2$.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

Any of the groups described herein may be unsubstituted or optionally substituted. When modifying a particular group, "substituted" means that the group the term modifies may, but does not have to, be substituted. Substitutions typically replace an available hydrogen with an alkyl, alkenyl, alkynyl, aryl, heteroaryl, aralkyl, alkylaryl, heteroaralkyl, heteroaralkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl) benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A triterpenoid compound of this invention may be administered in a pharmaceutical composition by various routes including, but not limited to, oral, subcutaneous, intravenous, or intraperitoneal administration (e.g. by injection). Depending on the route of administration, the active compound may be coated in a material to protect the compound from the action of acids and other natural conditions which may inactivate the compound.

For example, to administer the therapeutic compound by other than parenteral administration, it may be necessary to coat the compound with, or co-administer the compound with, a material to prevent its inactivation. By way of illustration, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

One or more triterpenoid compounds of the invention are administered at a therapeutically effective dosage sufficient to treat a condition in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans The triterpenoid compounds of the invention are of use in modulating IFN-γ-induced NO production in macrophages, said composition having an $IC_{50}$ value of at least less than 0.6 µM, more preferably less than 0.001 µM.

In one embodiment, the instant triterpenoid compounds are of use in a method of modulating excessive nitric oxide or prostaglandin formation in a subject by administering to a subject a pharmaceutically effective amount of one or more triterpenoid compounds, such that the nitric oxide or prostaglandin formation is modulated.

In a further embodiment, the triterpenoid compounds of the invention are of use in a method of preventing or treating a disorder characterized by overexpression of iNOS or COX-2 genes, wherein the method includes administering to a subject a pharmaceutically effective amount of one or more triterpenoid compounds, such that the disorder is prevented or treated. In a preferred embodiment, the disorder includes cancer, diabetic nephropathy, neurodegenerative disease, rheumatoid arthritis, inflammatory bowel disease, and other diseases whose pathogenesis is believed to involve excessive production of either nitric oxide or prostaglandins. In a particular embodiment, the neurodegenerative disease includes Parkinson's disease, Alzheimer's disease, multiple sclerosis, and amyotrophic lateral sclerosis. The cancer may include, e.g., a leukemic cancer or a solid cancer. A leukemic cancer is a cancer of a blood cell, a myeloid cell, a monocytic cell, a myelocytic cell, a promyelocytic cell, a myeloblastic cell, a lymphocytic cell, or a lymphoblastic cell. A solid cancer is a cancer of a bladder cell, a breast cell, a lung cell, a colon cell, a prostate cell, a liver cell, a pancreatic cell, a stomach cell, a testicular cell, a brain cell, an ovarian cell, a skin cell, a brain cell, a bone cell, or a soft tissue cell.

Moreover, the invention provides methods for the treatment and prevention of graft versus host disease (GVHD) by providing a triterpenoid compound of the invention either alone or in conjunction with another agent, such as an immunosuppressive agent such as a corticosteroid or tacrolimus, or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, it is contemplated that the instant triterpenoid compounds can be used to provide therapy for graft versus host diseases.

The practice of the methods of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Genetics; Molecular Cloning A Laboratory Manual, 2nd Ed., ed. by Sambrook, J. et al. (1989) Cold Spring Harbor Laboratory Press; Short Protocols in Molecular Biology, 3rd Ed., ed. by Ausubel, F. et al. (1995) Wiley, NY; DNA Cloning, Volumes I and II (D. N. Glover ed., 1985); Oligonucleotide Synthesis (M. J. Gait ed. (1984)); Mullis et al. U.S. Pat. No. 4,683,195; Nucleic Acid Hybridization (B. D. Hames & S. J. Higgins eds. (1984)); the treatise, Methods In Enzymology (Academic Press, Inc., N.Y.); Immunochemical Methods In Cell And Molecular Biology (Mayer and Walker, eds., Academic Press, London (1987)); Handbook Of Experimental Immunology, Volumes I-IV (D. M. Weir and C. C. Blackwell, eds. (1986)); and Miller, J. Experiments in Molecular Genetics (Cold Spring Harbor Press, Cold Spring Harbor, N.Y. (1972)).

The invention is described in greater detail by the following non-limiting examples.

Example 1

Synthesis of Triterpenoids

The triterpenoids of the invention can be generally produced from natural compounds such as oleanolic acid, ursolic acid, betulinic acid, or hederagenin, or derivatives thereof that include additional A and/or C ring modifications. Synthesis of the compounds can be achieved using any conventional method of synthesizing similar triterpenoids such as CDDO or CDDO-Me. See, e.g., U.S. Pat. No. 6,326,507, U.S. Pat. No. 6,552,075, U.S. Pat. No. 6,974,801, U.S. Pat. No. 7,288,568, U.S. Pat. No. 7,863,327, U.S. Pat. No. 7,915,402, U.S. Pat. No. 7,943,778, U.S. Pat. No. 8,034,955, U.S. Pat. No. 8,071,632, U.S. Pat. No. 8,124,656, U.S. Pat. No. 8,124,799, U.S. Pat. No. 8,129,429 and WO 2009/146216.

As one example, triterpenoid compounds of the invention can be synthesized by (a) methylating the carboxylic acid group of a compound of Formula III to afford a methyl ester (Formula IV); oxidizing the hydroxyl group of a compound of Formula IV with an oxidizing agent to form a double bond in Ring A (Formula V), epoxidating Ring C of the enone to form an epoxide, and forming a C-ring enol and halogenating the A-ring enone to yield a compound of Formula VI (Scheme 1)

SCHEME 1

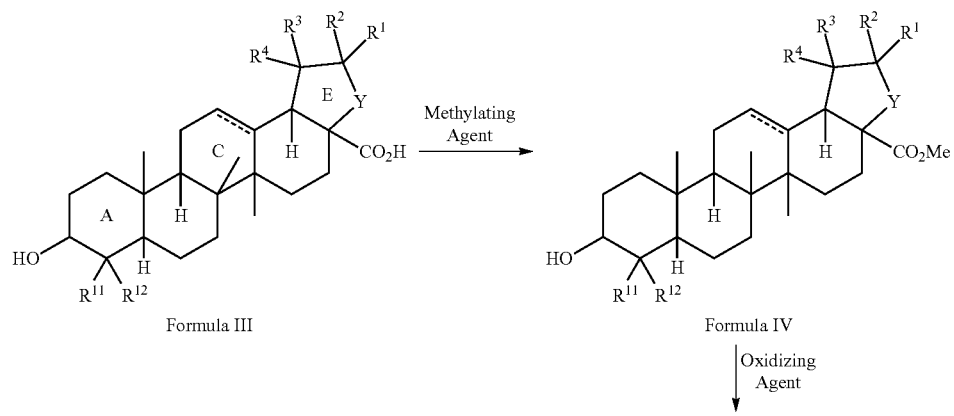

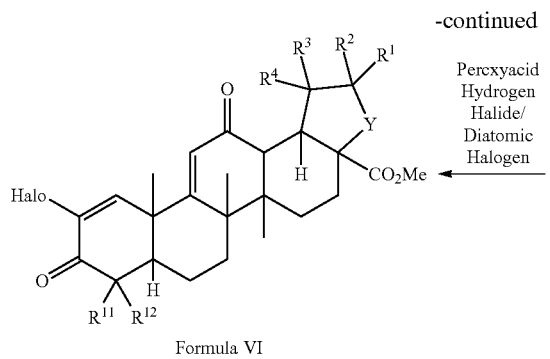

Formula VI

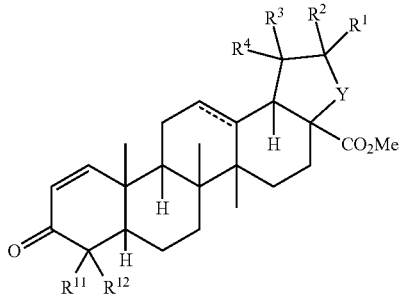

Formula V

According to this example, the methylating agent is an electrophilic methyl source including, but not limited to iodomethane, dimethyl sulfate, dimethyl carbonate, diazomethane, or with methylating reagents such as methyl triflate or methyl fluorosulfonate, optionally in the presence of a base such as $K_2CO_3$ or $Li_2CO_3$. Further, the oxidizing agent can be an iodine oxidizing agent such as o-iodoxybenzoic acid (IBX)(Nicolaou, et al. (2002) *J. Am. Chem. Soc.* 124: 2245-2258), diacetoxyiodobenzene (DAIB), fluorous DAIB (F-DAIB), Dess-Martin-Periodinane (DMP), or a stabilized formulation of IBX (SIBX; Ozanne, et al. (2003) *Org. Lett.* 5:2903) in one or a combination of suitable solvents such as DMSO and phenyl fluoride (fluorobenzene). Furthermore, epoxidation of Ring C can be carried out with an oxidant such as a peroxyacid, e.g., meta-chloroperoxybenzoic acid (mCPBA), peroxyacetic acid, or potassium peroxymonosulfate (Oxone). Acid catalyzed opening of the epoxide and bromination of the A Ring can be achieved with a hydrogen halide such as (HBr or HI) and a diatomic halogen molecule such as $Br_2$ or $I_2$.

As used in the context of the present invention, Formula III includes naturally occurring starting materials such as oleanolic acid, ursolic acid, betulinic acid, or hederagenin, or derivatives thereof.

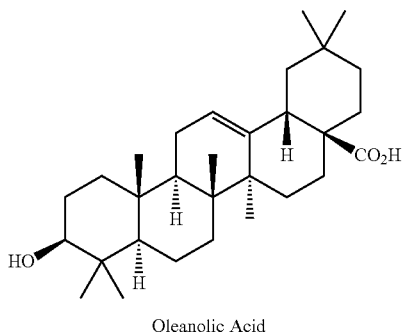

Oleanolic Acid

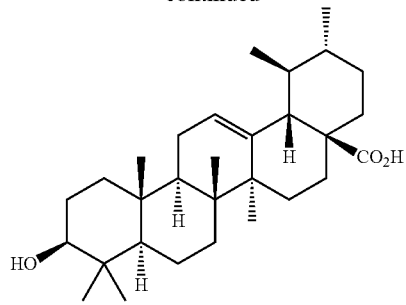

Ursolic Acid

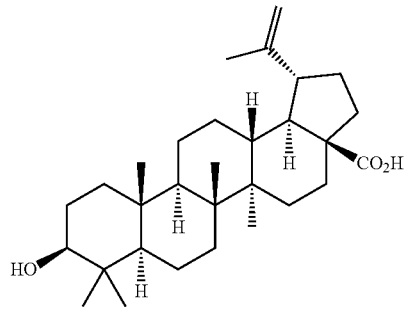

Betulinic Acid

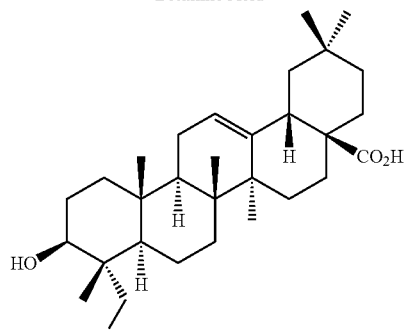

Hederagenin

As a specific example of using this synthetic method in the synthesis of triterpenoids, CDDO-Me was synthesized from oleanolic acid. As shown in Scheme 2, the natural triterpenoid oleanolic acid (1) was used as the starting material in the synthesis of CDDO-Me. The method commences with methylation of the carboxylic acid of oleanolic acid (1) to afford methyl ester 2 in quantitative yield. With ester 2, activation of the A-ring is fulfilled by 2-iodoxybenzoic acid-mediated two-fold oxidation to give enone 3. Epoxidation with meta-chloroperoxybenzoic acid, followed by direct C-ring enolization and A-ring enone bromination with bromine and hydrobromic acid, affords key intermediate 4. With bromide 4 in hand, a cross-coupling reaction with copper cyanide provides CDDO-Me (5) (Scheme 2). Intermediate 4 was prepared in high yield and few overall steps, thereby providing a base compound for development of the analogs and derivatives described herein.

SCHEME 2

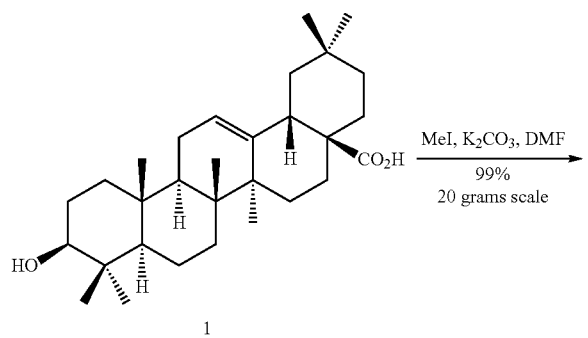

1

MeI, $K_2CO_3$, DMF
99%
20 grams scale

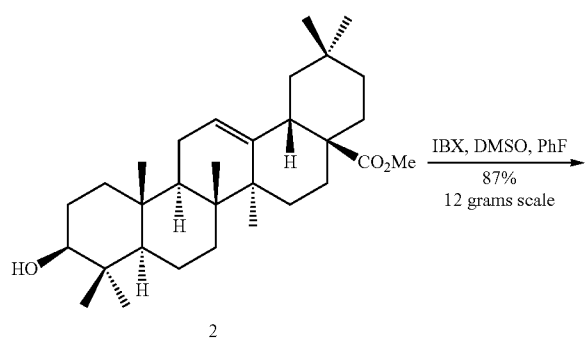

2

IBX, DMSO, PhF
87%
12 grams scale

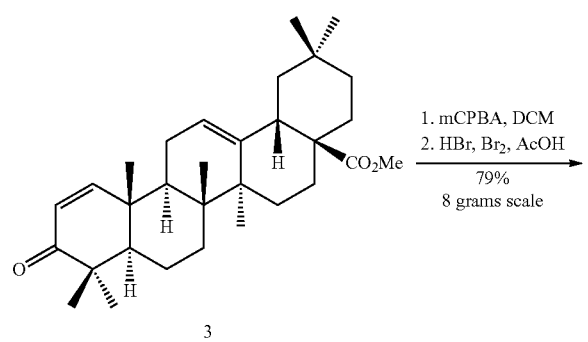

3

1. mCPBA, DCM
2. HBr, $Br_2$, AcOH
79%
8 grams scale

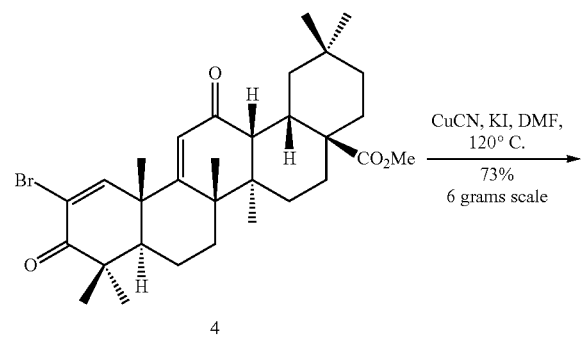

4

CuCN, KI, DMF, 120° C.
73%
6 grams scale

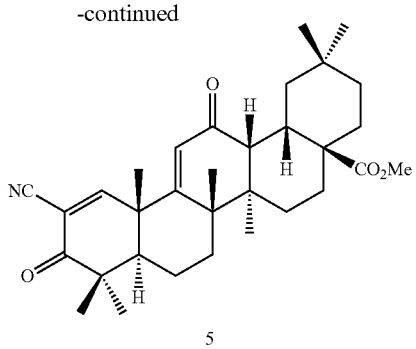

5

Unless otherwise specified, the reagents used in the instant methods are conventionally known in the art. For example, MeI refers to methyl iodide, DMF refers to dimethylformamide, IBX is 2-iodoxybenzoic acid, DMSO is dimethyl sulfoxide, PhF is phenyl fluoride, mCPBA refers to meta-chloroperoxybenzoic acid, HBr is hydrogen bromide, DCM is dichloromethane, AcOH is acetic acid, and CuCN is copper cyanide.

Example 2

Ring A Modifications

Given the reactivity of Ring A halogen, Formula VI serves as a substrate for the synthesis of the triterpenoid derivatives of the invention. For example, contact of a compound of Formula VI with a cyanide ion source such as $K_4[Fe(CN)_6]$, KCN, NaCN, ZnCN, CuCN, $(CH_3)_2C(-OH)CN$ or TMSCN results in the displacement of the aromatic halide with a cyanide ion. In other embodiments, the compound of Formula VI can be reacted with a wide variety of reagents to replace the halogen on Ring A. For example, the compound of Formula VI can be aminated or coupled or cross-coupled with an alkyl, alkenyl, alkynyl or aryl group to provide a variety of substituents on Ring A. For example, Formula VI can be aminated via Buchwald-Hartwig amination (Buchwald & Muci (2002) Top. Curr. Chem. 219:133-209; Hartwig (1999) Pure Appl. Chem. 71:1417; Buchwald & Yang (1999) J. Orgmet. Chem. 576:125; Hartwig (1998) ACIEE 37:2046; Hartwig (1998) Acc. Chem. Res. 31:852; Buchwald et al. (1998) Acc. Chem. Res. 31:805) to provide amides and amines 6 ($R^{16}$=H and $R^{17}$=H or CHO). Moreover, when 6 is a formamide ($R^{16}$=H and $R^{17}$=CHO), isonitrile 7 can be readily synthesized under mild conditions (Porcheddu, et al. (2005) J. Org. Chem. 70:2361-3). In addition, Sonogashira coupling (Sonogashira, et al. (1975) Tetrahedron Lett. 16:4467-70) provides alkynes 8 and 10. Likewise, Suzuki (Miyuara, et al. (1979) Tetrahedron Lett. 20:3437-40; Miyaura & Suzuki (1979) Chem. Comm. 19:866-7; Miyaura & Suzuki (1995) Chem. Rev. 95:2457-2483), Stifle (Kosugi, et al. (1977) Chem. Lett. 301; Milstein & Stille (1978) J. Am. Chem. Soc. 100:3636), and Negishi (King, et al. (1977) J. Chem. Soc. Chem. Commun. 19:683) cross-coupling reactions provide compounds having the structure of compound 9 and dimers such as compounds 10-17 are readily produced when the halogen of Formula VI is iodide.

6
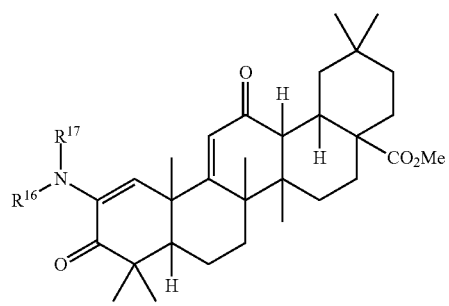
7
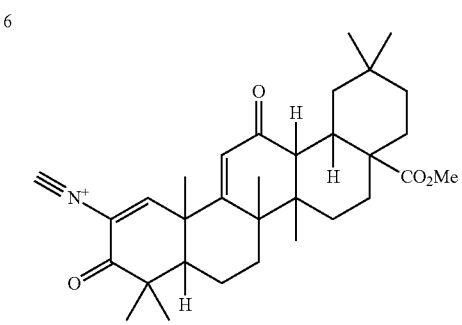
8
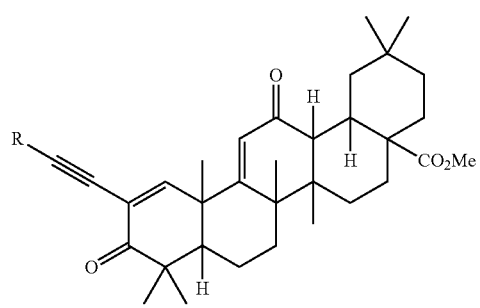
(R = alkyl, aryl, alkenyl, alkynyl)
9
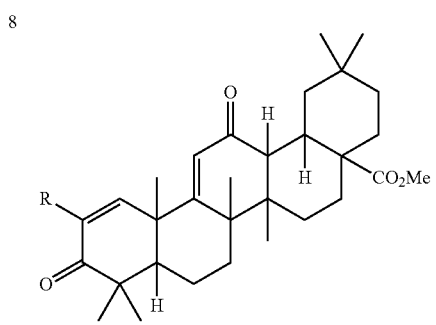
(R = alkyl, aryl, alkenyl, alkynyl)
10
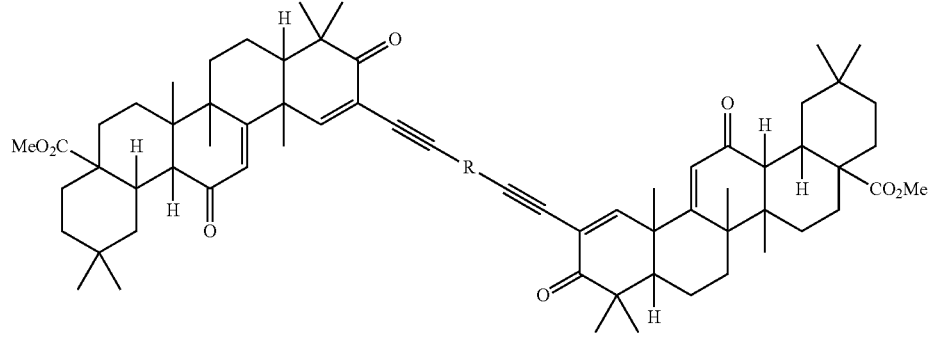
(R = alkyl, aryl, alkenyl, alkynyl
11
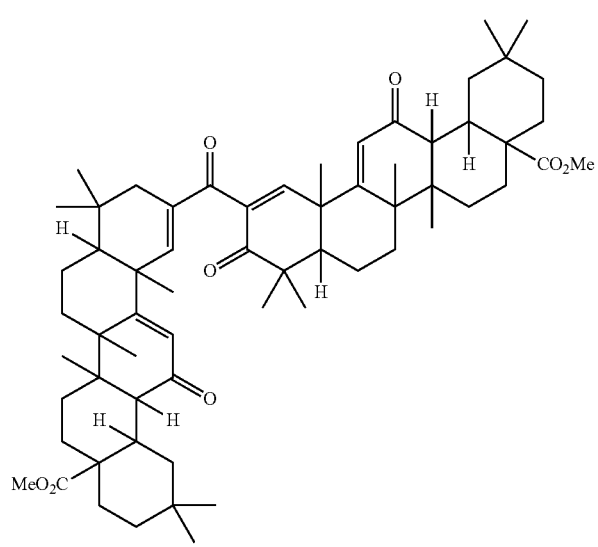

12
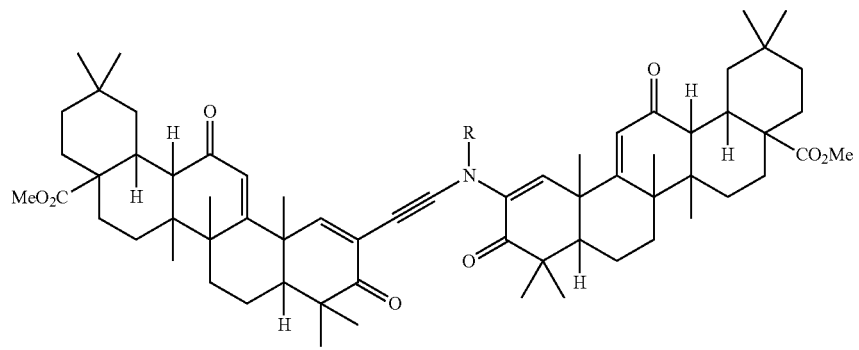
(R = H, alkyl, aryl, alkenyl, alkynyl)
13
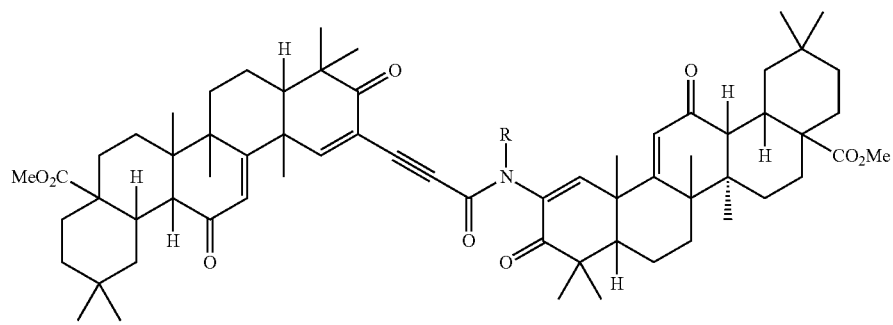
(R = H, alkyl, aryl, alkenyl, alkynyl)
14
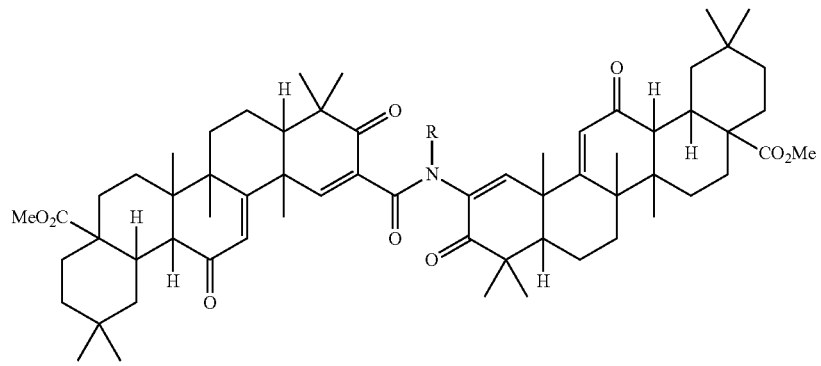
(R = H, alkyl, aryl, alkenyl, alkynyl)
15
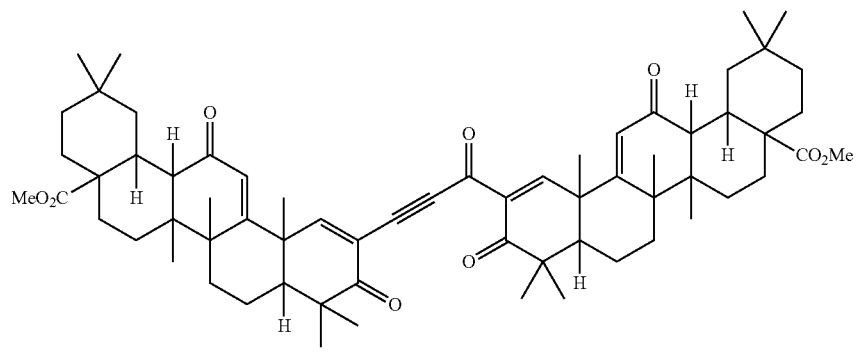

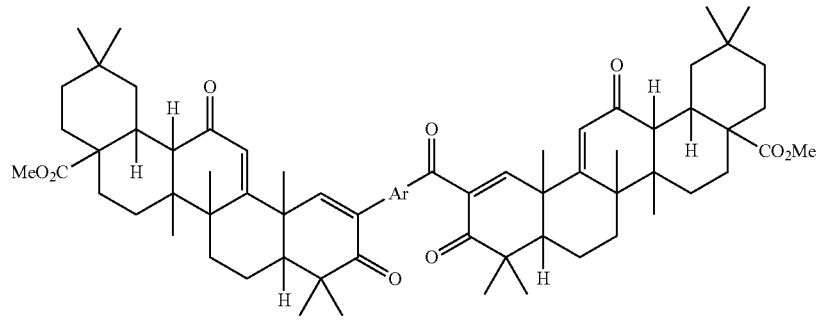

16

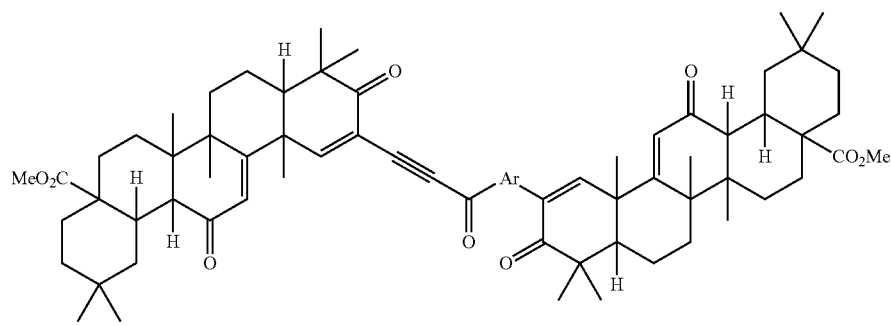

17

Example 3

Derivatives with Modifications at C-17

Amides (Formula VI), ethers (Formula VII), and esters (Formula VIII and Formula IX) are readily obtained using the instant method in combination with techniques known in the art. See U.S. Pat. No. 6,974,801 and US 2008/0233195.

Formula VI

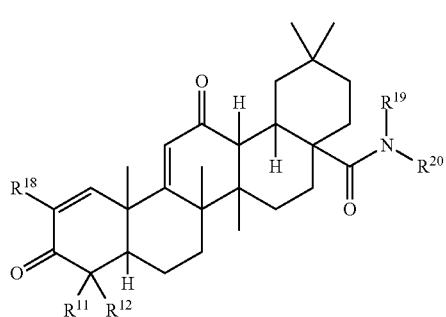

Formula VII

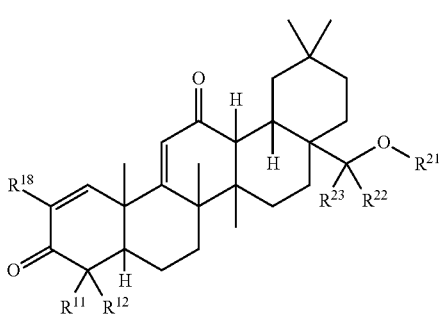

Formula VIII

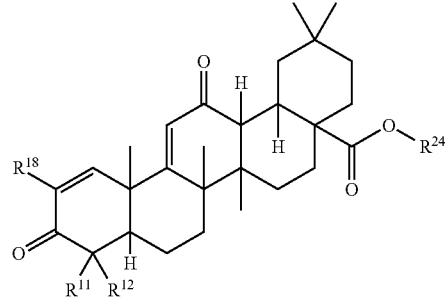

Formula IX

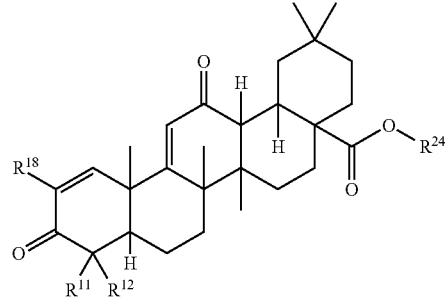

In accordance with Formulae VI-IX, $R^{11}$ and $R^{12}$ are as defined for Formula I;

$R^{18}$ is —OMs, —$CH_2$OMs, —C(=O)C≡C$R^a$, —C≡CCO$_2R^a$, —C≡CSO$_2R^a$, —C≡CC(=O)$R^a$, —SO$_2R^a$, =O or =CR$^c$R$^d$, wherein $R^d$ is hydrogen, halo, alkylthiyl, or substituted or unsubstituted alkylsulfonyl or alkylsulfonyl-O—;

$R^{22}$ and $R^{23}$ are independently a hydrogen, hydroxyl, halo, alkyl, nitro or amino group;

$R^{19}$, $R^{20}$, $R^{21}$, $R^{24}$ and $R^{25}$ are independently a hydrogen, hydroxyl, —$NR^fR^g$, cyano, halo, azido, phosphate, 1,3-dioxoisoindolin-2-yl, mercapto, silyl or —COOH group, substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-acylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups, a —$CO_2Me$, carbonyl imidazole, —CO-D-Glu(OAc)$_4$, —$CONH_2$, —$CONHNH_2$, —$CONHCH_2CF_3$, or —C(=O)-heteroaryl group.

Example 4

CDDO-Me Derivatives with A-Ring Modifications

CDDO-Me derivatives within the scope of Formula and containing A-Ring modifications are as follows.

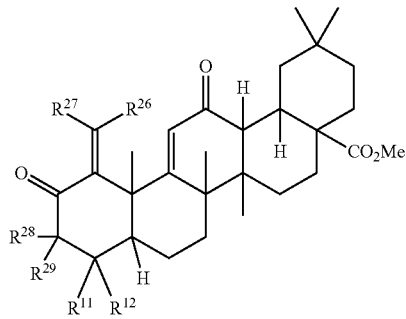

Formula X

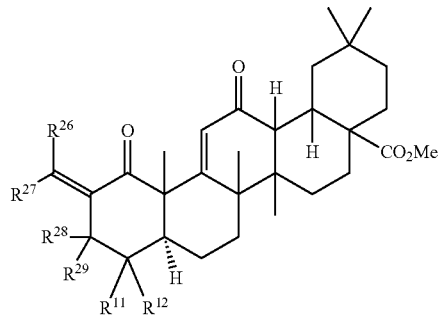

Formula XI

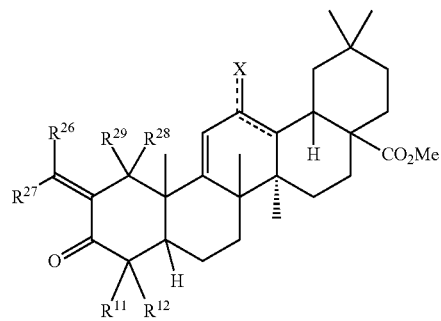

Formula XII

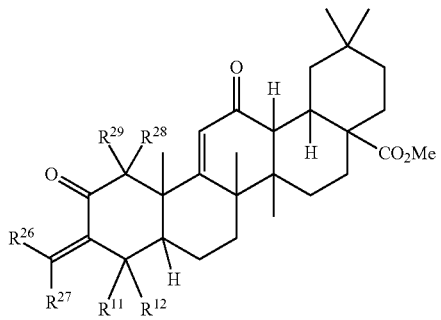

Formula XIII

In accordance with Formulae X-XIII, $R^{11}$ and $R^{12}$ are as defined for Formula I;

X is =O or —OMe;

dashed bonds are present or absent;

$R^{26}$ and $R^{27}$ are independently a hydrogen, halo (e.g., Cl or F), alkylthiyl, or substituted or unsubstituted alkylsulfonyl or alkylsulfonyl-O—;

$R^{28}$ and $R^{29}$ are independently —H, or together are =O.

Exemplary compounds of Formulae X-XIII include compounds 18-82:

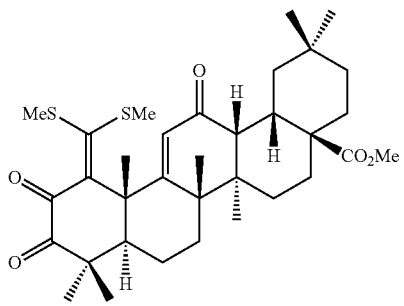

18

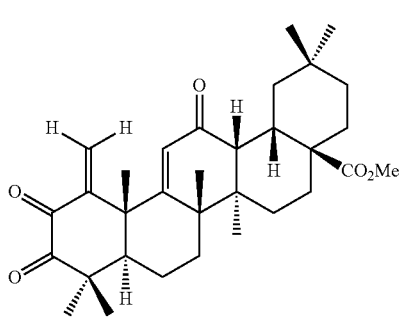

19

20
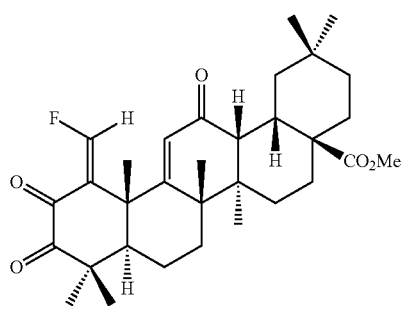
21
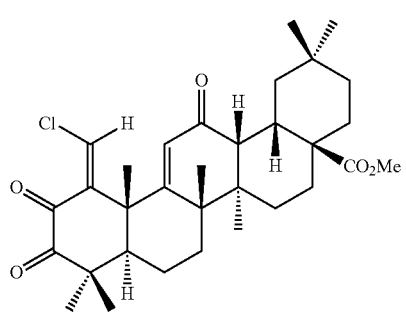
22
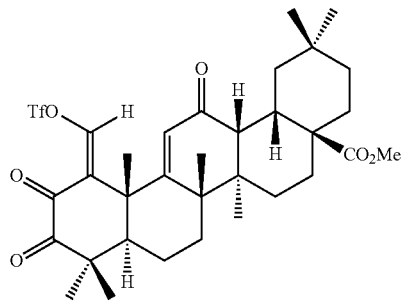
23
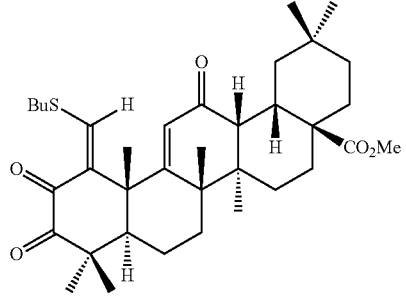
24
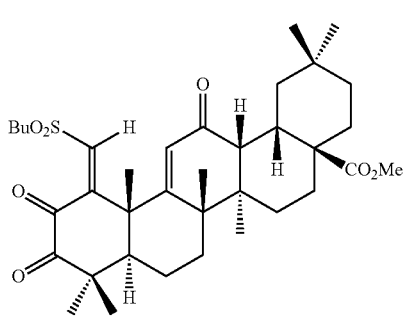
25
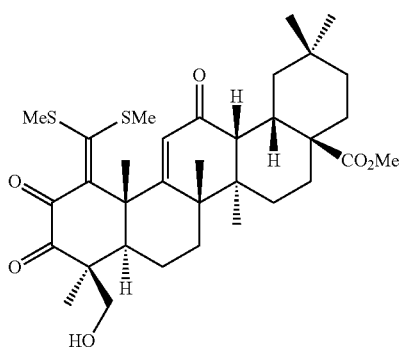
26
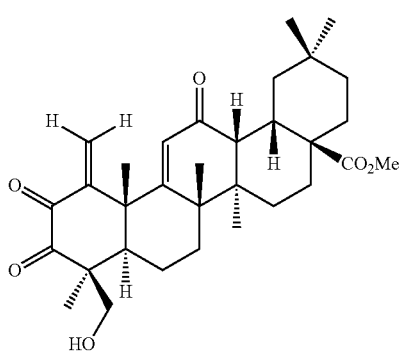
27
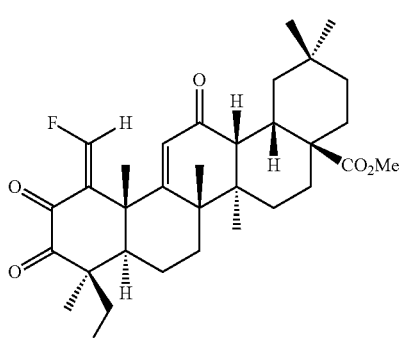
28
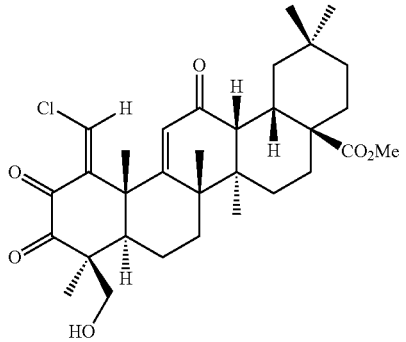

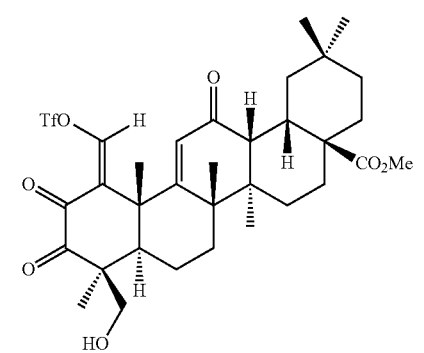
29
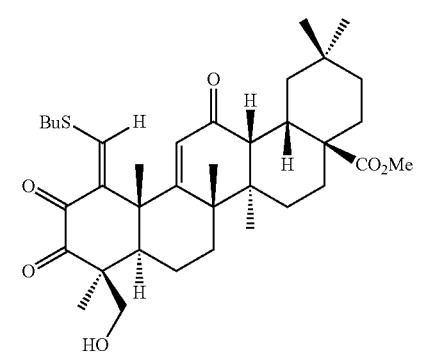
30
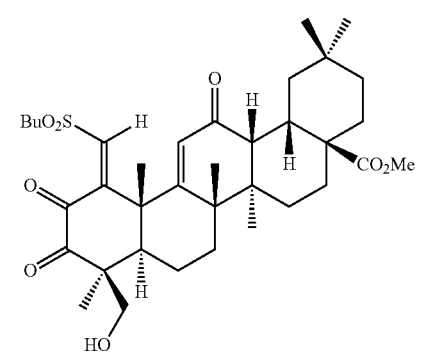
31
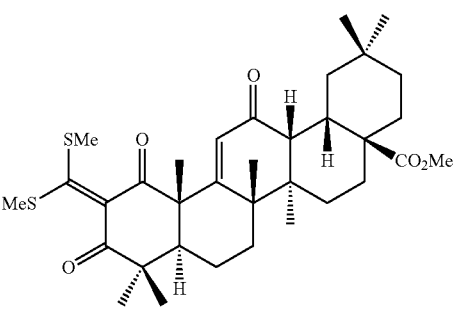
32
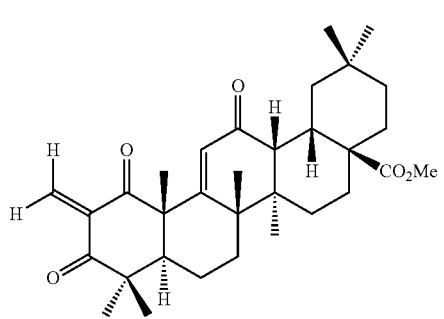
33
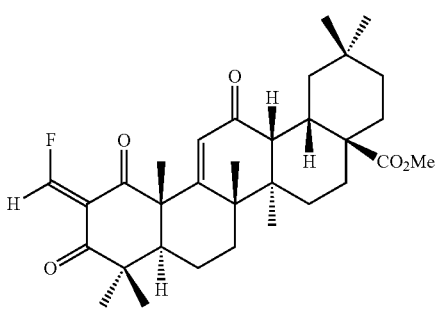
34
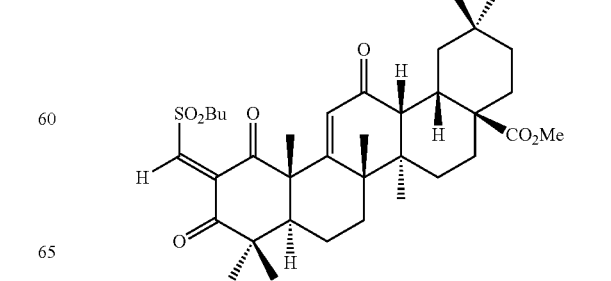

31
-continued
39
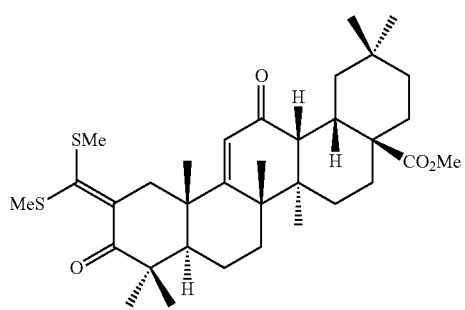
40
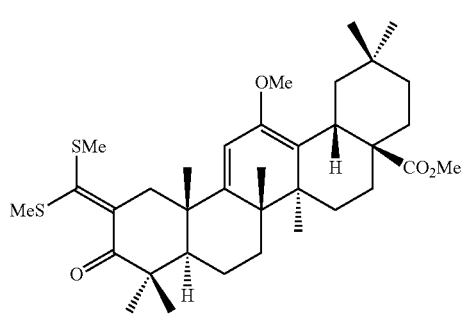
41
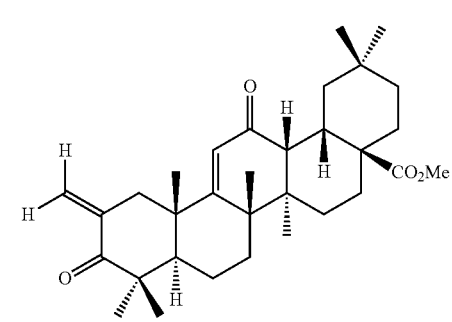
42
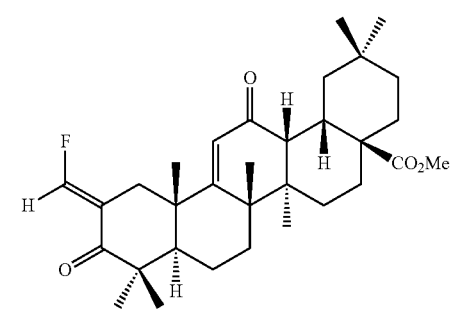
43
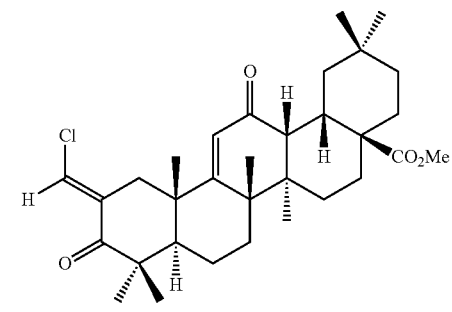
32
-continued
44
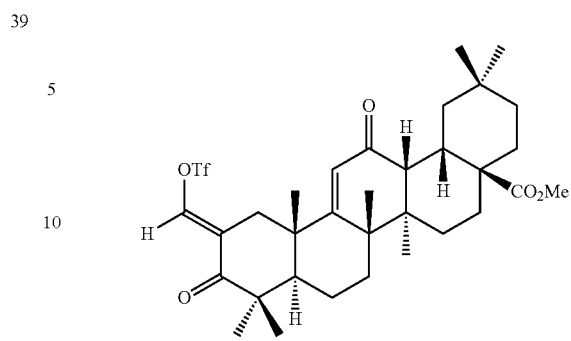
45
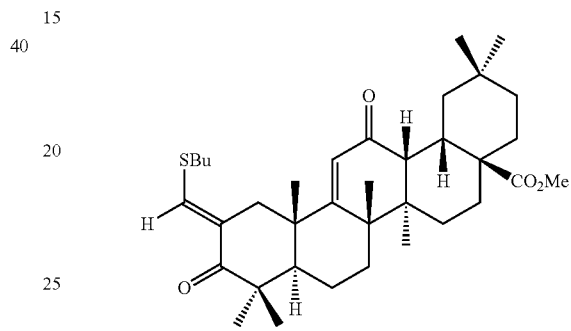
46
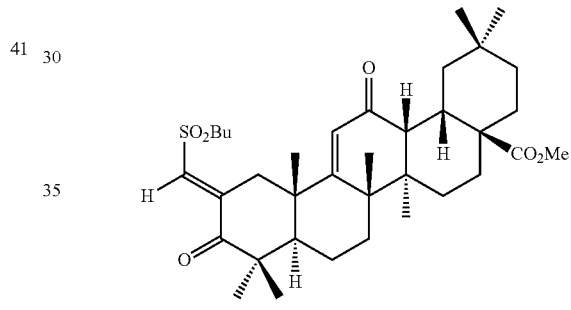
47
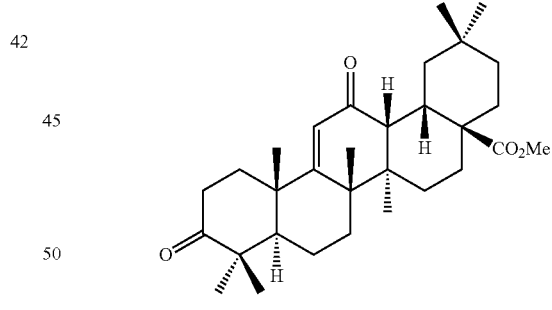
48
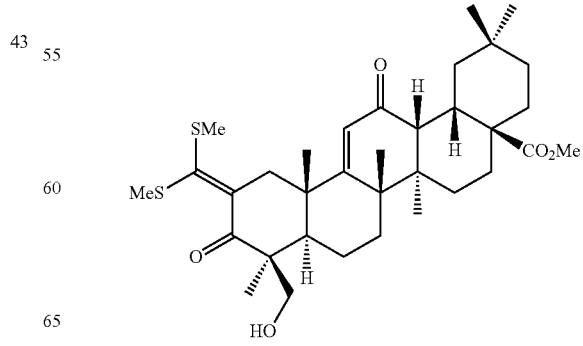

49
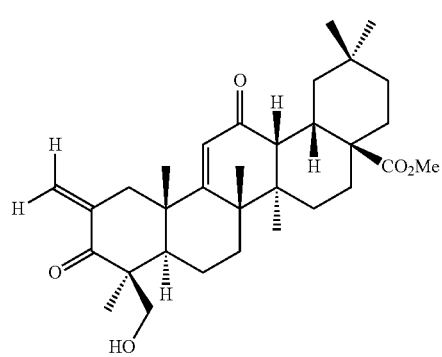
50
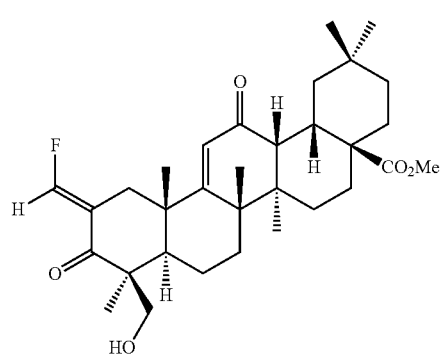
51
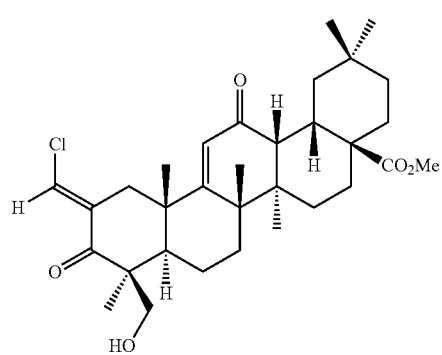
52
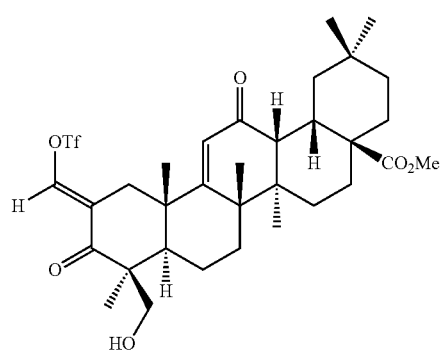
53
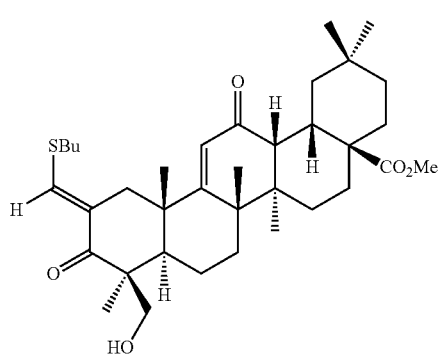
54
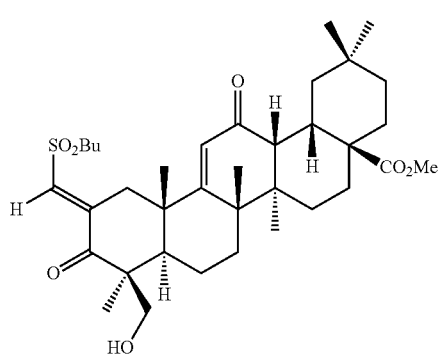
55
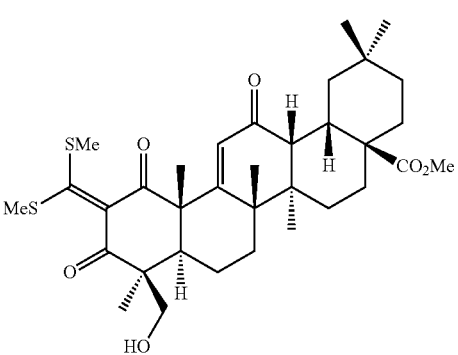
56
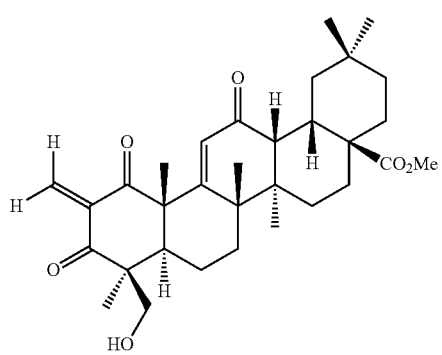

-continued
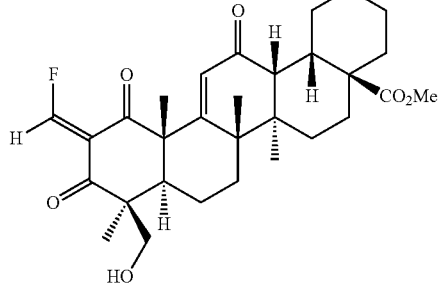
57
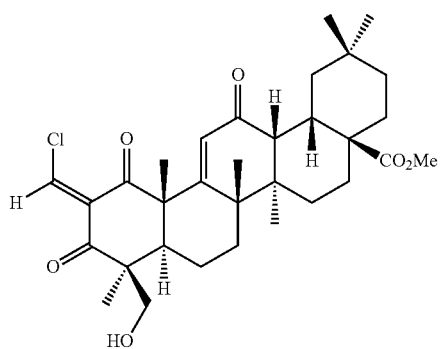
58
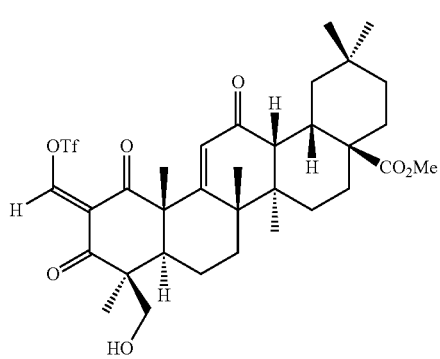
59
60
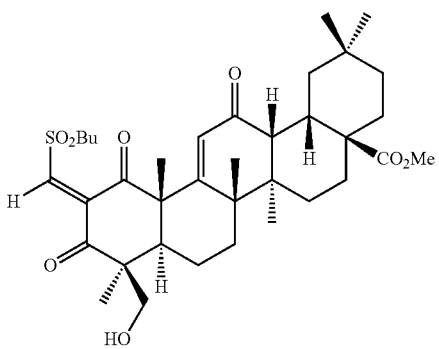
61
Example 5
Mesylate Derivatives of CDDO-Me
Mesylate derivatives of CDDO-Me of Formula XIV-XVI are also included with the scope of this invention.
Formula XIV
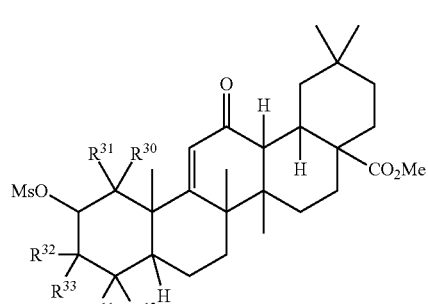
Formula XV
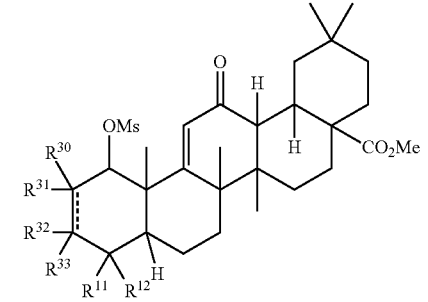
Formula XVI
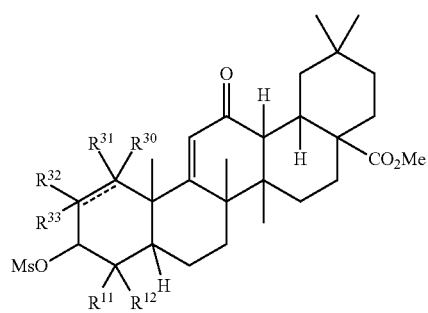
In accordance with Formulae XIV-XVI:
$R^{11}$ and $R^{12}$ are as defined for Formula I;
$R^{30}$, $R^{31}$, $R^{32}$ and $R^{33}$ are each independently a hydrogen, cyano, —OMs, or —CH$_2$OMs group; or $R^{30}$ and $R^{31}$ or $R^{32}$ and $R^{33}$ together are $=CH_2$; and dashed bonds are either present or absent.
Exemplary compounds of Formulae XIV-XVI include compounds 62-75:
62
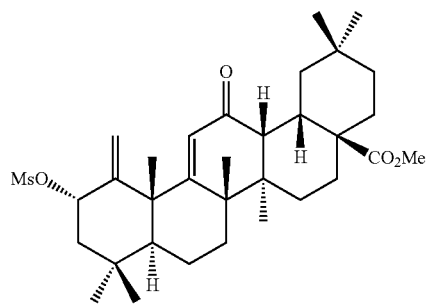
63
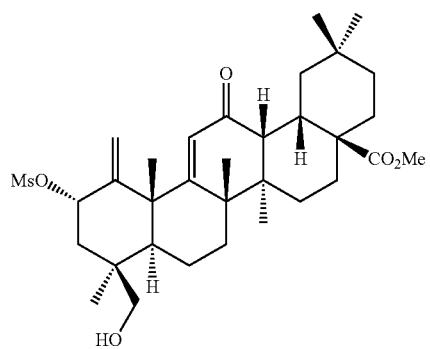
64
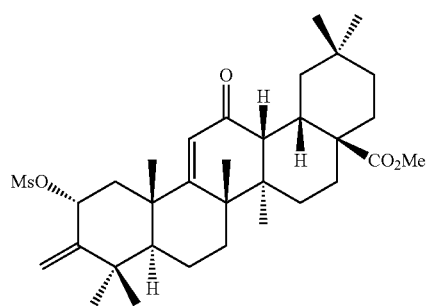
65
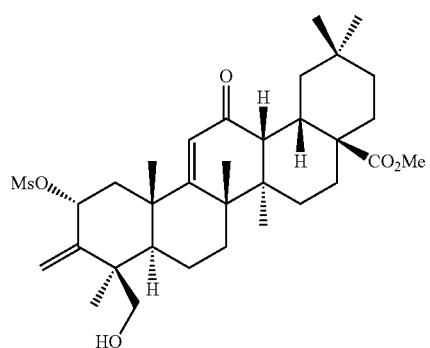
66
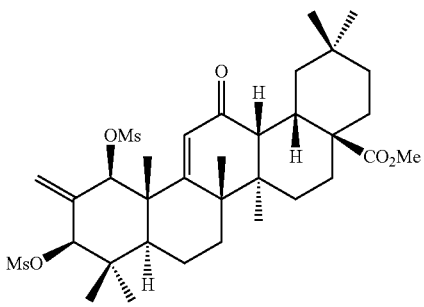
67
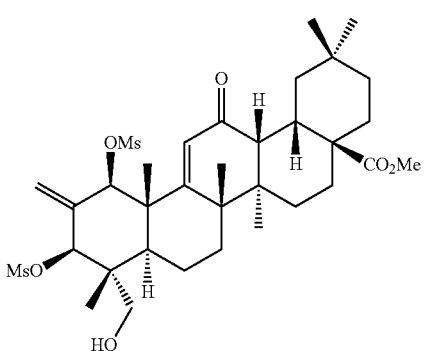
68
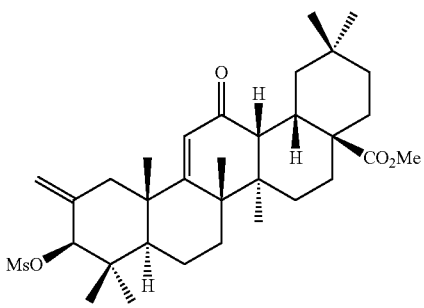
69
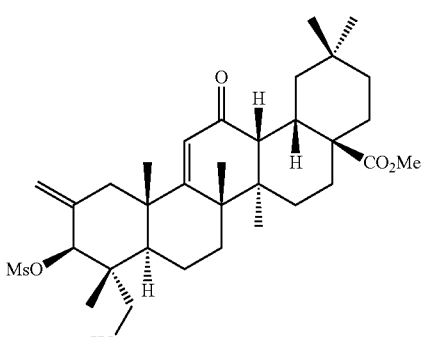
70
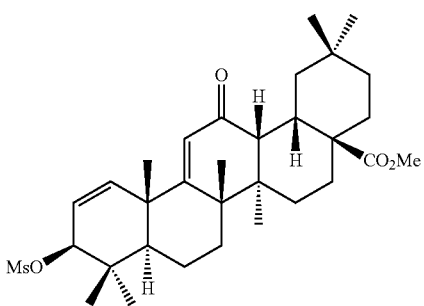

71

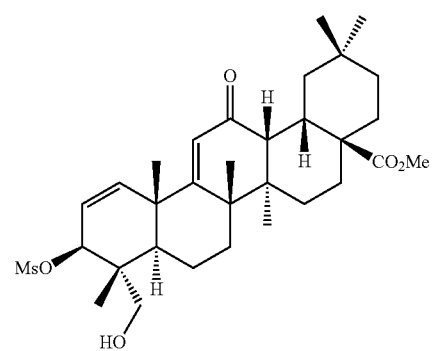

72

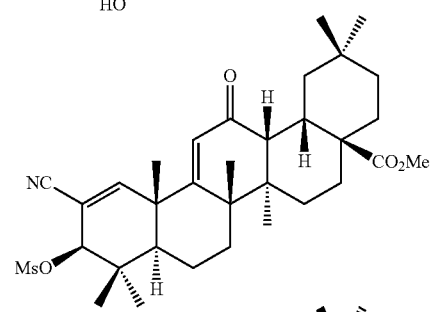

73

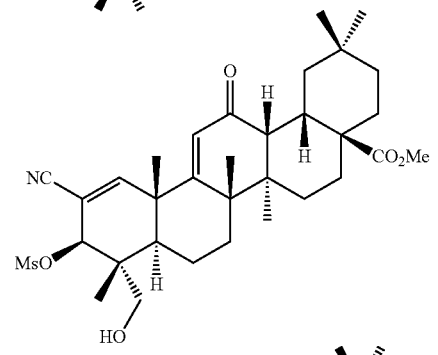

74

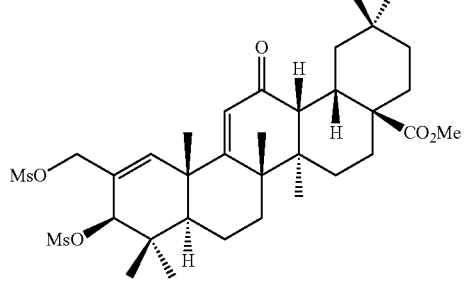

75

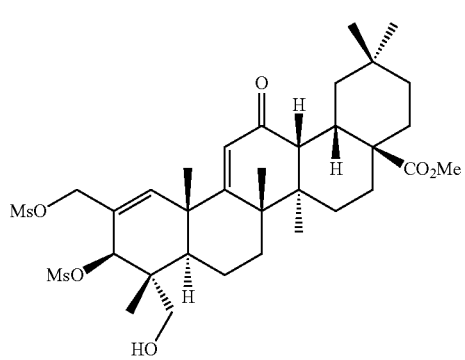

Mesylate derivatives having the structure of Formula XVII are also embodied by the present invention.

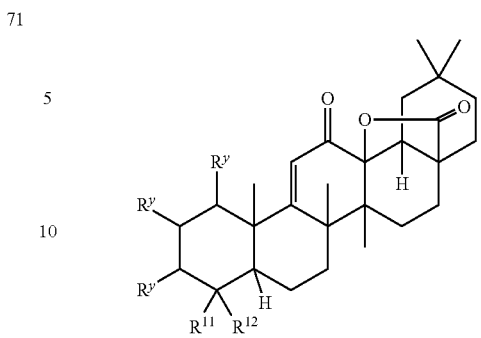

Formula XVII wherein $R^{11}$ and $R^{12}$ are as defined for Formula I; and at least one of $R^y$ is OMs and the remaining $R^y$ are a hydrogen, cyano, —OMs, —CH$_2$OMs, or =CH$_2$ group.

What is claimed is:

1. A triterpenoid compound of the structure of Formula X, Formula XI, Formula XII or Formula XIII:

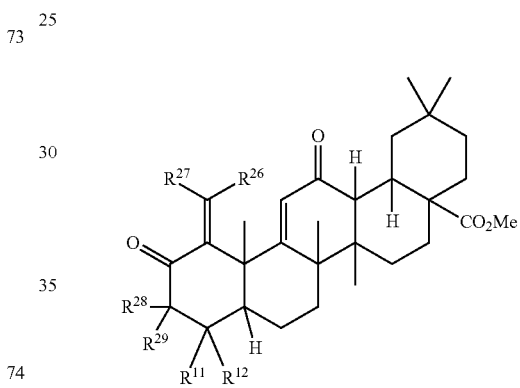

Formula X

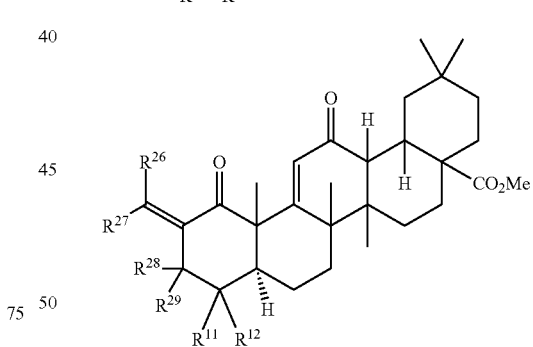

Formula XI

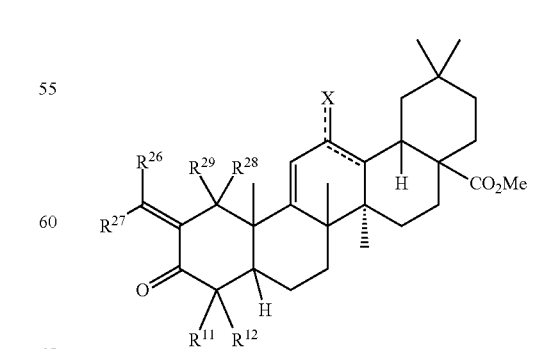

Formula XII

Formula XIII

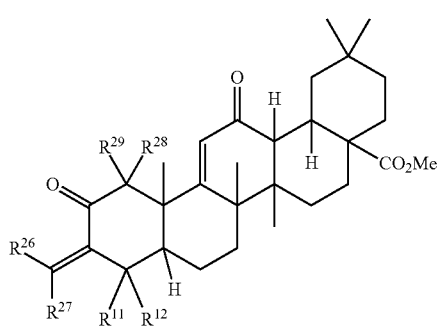

R$^{11}$ and R$^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or R$^{11}$ and R$^{12}$ are taken together and are alkanediyl, alkenediyl, arenediyl, alkoxydiyl, alkenyloxydiyl, alkylaminodiyl, alkenylaminodiyl, or alkenylaminooxydiyl;

X is =O or —OMe;

dashed bonds are present or absent;

R$^{26}$ and R$^{27}$ are independently a hydrogen, halo, alkylthiyl, or substituted or unsubstituted alkylsulfonyl or alkylsulfonyl-O—; and R$^{28}$ and R$^{29}$ are independently —H, or together are =O.

2. A pharmaceutical composition comprising the compound of claim 1 in admixture with a pharmaceutically acceptable carrier.

* * * * *